(12) United States Patent
Grant et al.

(10) Patent No.: US 11,723,863 B2
(45) Date of Patent: Aug. 15, 2023

(54) ORAL CARE COMPOSITIONS COMPRISING BENZOCAINE AND MUCOADHESIVE THIN FILMS FORMED THEREFROM

(71) Applicant: Church & Dwight Co., Inc., Princeton, NJ (US)

(72) Inventors: Sarah Lindsay Grant, Scotland (GB); Dominic Gregory Walsh, Scotland (GB); Mark Alexander Livingstone, Scotland (GB)

(73) Assignee: Church & Dwight Co., Inc., Princeton, NJ (US)

( * ) Notice: Subject to any disclaimer, the term of this patent is extended or adjusted under 35 U.S.C. 154(b) by 23 days.

(21) Appl. No.: 17/400,407

(22) Filed: Aug. 12, 2021

(65) Prior Publication Data

US 2021/0369602 A1 Dec. 2, 2021

Related U.S. Application Data

(63) Continuation of application No. 16/446,835, filed on Jun. 20, 2019, now abandoned.

(60) Provisional application No. 62/698,706, filed on Jul. 16, 2018.

(30) Foreign Application Priority Data

Jun. 22, 2018 (GB) .................................. 1810299

(51) Int. Cl.
| | | |
|---|---|---|
| *A61K 9/00* | (2006.01) | |
| *A61K 31/195* | (2006.01) | |
| *A61K 47/10* | (2017.01) | |
| *A61K 9/70* | (2006.01) | |
| *A61K 47/38* | (2006.01) | |
| *A61K 47/02* | (2006.01) | |
| *A61K 47/32* | (2006.01) | |

(52) U.S. Cl.
CPC ............ *A61K 9/006* (2013.01); *A61K 9/7015* (2013.01); *A61K 31/195* (2013.01); *A61K 47/02* (2013.01); *A61K 47/10* (2013.01); *A61K 47/32* (2013.01); *A61K 47/38* (2013.01)

(58) Field of Classification Search
CPC ...... A61K 9/5036; A61K 9/0095; A61K 9/19; A61K 9/5031; A61K 39/145; A61K 39/235
See application file for complete search history.

(56) References Cited

U.S. PATENT DOCUMENTS

| | | | |
|---|---|---|---|
| 5,192,802 | A | 3/1993 | Rencher |
| 5,234,957 | A | 8/1993 | Mantelle |
| 5,446,070 | A | 8/1995 | Mantelle |
| 5,700,478 | A | 12/1997 | Biegajski et al. |
| 5,948,430 | A | 9/1999 | Zerbe et al. |
| 6,072,100 | A | 6/2000 | Mooney et al. |
| 6,177,096 | B1 | 1/2001 | Zerbe et al. |
| 6,284,264 | B1 | 9/2001 | Zerbe et al. |
| 6,375,963 | B1 | 4/2002 | Repka et al. |
| 6,709,671 | B2 | 3/2004 | Zerbe et al. |
| 6,800,329 | B2 | 10/2004 | Horstmann et al. |
| 6,887,307 | B1 | 5/2005 | Scott et al. |
| 7,579,019 | B2 | 8/2009 | Tapolsky et al. |
| 7,666,337 | B2 | 2/2010 | Yang et al. |
| 7,897,080 | B2 | 3/2011 | Yang et al. |
| 7,972,618 | B2 | 7/2011 | Fuisz et al. |
| 8,603,514 | B2 | 12/2013 | Yang et al. |
| 8,652,378 | B1 | 2/2014 | Yang et al. |
| 8,658,201 | B2 | 2/2014 | Singh et al. |
| 8,765,167 | B2 | 7/2014 | Myers |
| 8,900,497 | B2 | 12/2014 | Yang |
| 8,906,277 | B2 | 12/2014 | Yang et al. |
| 9,144,552 | B2 | 9/2015 | Singh et al. |
| 9,486,543 | B2 | 11/2016 | Skigen |
| 2001/0022964 | A1 | 9/2001 | Leung et al. |
| 2004/0202698 | A1 | 10/2004 | Ramji et al. |
| 2005/0031675 | A1 | 2/2005 | Leung et al. |
| 2006/0073174 | A1 | 4/2006 | Moro et al. |
| 2006/0182786 | A1 | 8/2006 | Rademacher |
| 2009/0099149 | A1 | 4/2009 | Liu et al. |
| 2009/0246257 | A1 | 10/2009 | Modi |
| 2010/0055055 | A1 | 3/2010 | Albeck et al. |
| 2012/0114705 | A1 | 5/2012 | Zerbe et al. |
| 2014/0120150 | A1 | 5/2014 | McDonald, III et al. |
| 2015/0104493 | A1 | 4/2015 | McDonald, III et al. |
| 2016/0030579 | A1 | 2/2016 | Carty |
| 2017/0027857 | A1 | 2/2017 | Skigen |

FOREIGN PATENT DOCUMENTS

| | | |
|---|---|---|
| CN | 103142562 | 6/2013 |
| EP | 0250187 | 12/1987 |

(Continued)

OTHER PUBLICATIONS

Bala, "Orally Dissolving strips: A new approach to oral drug delivery system," International Journal of Pharmaceutical Investigation (Apr. 2013); 3(2).

(Continued)

*Primary Examiner* — Susan T Tran
*Assistant Examiner* — William Craigo
(74) *Attorney, Agent, or Firm* — Church & Dwight Co., Inc.

(57) ABSTRACT

The present invention provides oral care compositions. The compositions may be provided in a solid form, such as a film. The compositions can comprise one or more film forming polymers, one or more bioadhesive agents, one or more plasticizers, benzocaine (and optionally one or more further active ingredients), one or more polymeric solvents, and an aqueous solvent. The oral care composition can be a solid or semi-solid composition up to a temperature of at least 40° C. Methods of providing such an oral care compositions are also provided herein.

15 Claims, No Drawings

(56) References Cited

FOREIGN PATENT DOCUMENTS

| | | |
|---|---|---|
| EP | 2431028 | 3/2012 |
| EP | 1504765 | 7/2015 |
| EP | 2889030 | 7/2015 |
| EP | 3111929 A1 | 1/2017 |
| EP | 3111929 B1 | 8/2018 |
| WO | WO92/15289 | 9/1992 |
| WO | WO 2002/043657 | 6/2002 |
| WO | WO 2004/045537 | 6/2004 |
| WO | WO 2011/153334 | 12/2011 |
| WO | WO 2012/169417 | 12/2012 |
| WO | WO 2013/162404 | 10/2013 |
| WO | WO 2014/070485 | 5/2014 |
| WO | WO 2015/195605 | 12/2015 |
| WO | WO 2016/094567 | 6/2016 |
| WO | WO 2018/004576 | 1/2018 |
| WO | WO 2018/029671 | 2/2018 |

OTHER PUBLICATIONS

Chun, "Preparation of Buccal Patch Composed of Carbopol, Poloxamer and Hydroxypropyl Methylcellulose," Arch Pharm Res 26(11), 2003, 973-78.

ORAL CARE COMPOSITIONS COMPRISING BENZOCAINE AND MUCOADHESIVE THIN FILMS FORMED THEREFROM

CROSS-REFERENCE TO RELATED APPLICATIONS

This application is a continuation of U.S. application Ser. No. 16/446,835, filed Jun. 20, 2019, which claims priority to both U.S. Provisional Application No. 62/698,706, filed Jul. 16, 2018, and United Kingdom Application No. 1810299.6, filed Jun. 22, 2018, which applications are hereby incorporated by reference in their entirety in this application.

FIELD OF THE INVENTION

The present invention relates to oral compositions useful for providing pain relief, and more particularly to compositions suitable for formation of orally soluble, mucoadhesive thin films.

BACKGROUND

This invention relates to a pliable and soluble mucoadhesive oral composition that is capable of providing targeted and long-lasting delivery of active ingredients for the temporary relief of pain and various oral discomfort ailments including toothaches and mouth sores.

Current solutions for the topical treatment of toothaches and mouth sores are mainly delivered in the form of liquids, pastes, gels, patches, disks and pressed tablets. These forms often dissolve, spread easily, or get dislocated and cause numbness throughout the oral mucosa. Furthermore, the existing compositions generally provide only a short-term analgesic effect.

Accordingly, there is still a desire and a need to provide an oral care composition that enables the active ingredient(s) to be delivered locally to the treatment site through the oral composition in a much more targeted fashion. It is further desirable to provide an oral composition that provides a long-lasting pain relief compared to existing products.

SUMMARY OF THE INVENTION

The present disclosure relates to oral care compositions that comprise benzocaine as an active agent and that are either in a solid form or may be applied to form a substantially solid film inside the oral cavity. The solid composition is pliable, mucoadhesive, and slowly soluble within the oral cavity. The oral care compositions overcome deficiencies of the prior art and enable the active ingredient(s) to be delivered locally to the treatment site through the mucoadhesive oral composition in a much more targeted fashion. When applied at the treatment site, the oral care composition provides a long-lasting pain relief as compared to the existing products. The composition can be a solid or semi-solid dosage form and preferably is in the form of a film that can be easily molded around a tooth or onto another substantially uneven surface within the oral cavity to deliver an active ingredient, such as a pain reliever, thereto. It can provide good adhesion for maximum and targeted delivery of drug and hence, a more gradual coverage and longer duration of relief from pain and various oral discomfort ailments.

In one or more embodiments, the present disclosure particularly provides an oral care composition comprising: one or more film forming polymers in a total amount of about 40% to about 80% by weight; one or more bioadhesive agents in a total amount of about 0.5% to about 10% by weight; one or more plasticizers in a total amount of about 0.5% to about 8% by weight; one or more active agents in a total amount of about 2% to about 35% by weight, the one or more active agents including at least benzocaine; one or more polymeric solvents in which the one or more active agents is solubilized, the one or more polymeric solvents being in a total amount of about 5% to about 20% by weight; and an aqueous medium in an amount of about 0.5% to about 15% by weight; each of the foregoing amounts being based on the total weight of the oral care composition. The oral care composition preferably is in the form of a film having a thickness of about 100 µm to about 500 µm. In further embodiments, the oral care composition may be defined in relation to any one or more of the following statements, which can be combined in any order and number.

The one or more film forming polymers can comprise one or more of a polyvinylpyrrolidone, a polysaccharide, and a cellulose derivative.

The one or more film forming polymers can be selected from the group consisting of a polyvinylpyrrolidone, pullulan, hydroxypropyl cellulose, pectin, and combinations thereof.

The one or more film forming polymers can include a polyvinylpyrrolidone in an amount of about 20% to about 40% by weight and pullulan in an amount of about 20% to about 40% by weight, based on the total weight of the oral care composition.

The one or more bioadhesive agents can comprise one or more of a polycarbophil and a polyol.

The one or more plasticizers can include glycerol in an amount of about 0.25% to about 5% by weight, based on the total weight of the oral care composition.

The one or more active ingredients can further include menthol.

The one or more active ingredients can include benzocaine in an amount of about 2% to about 15% by weight and menthol in an amount of about 2% to about 20% by weight based on the total weight of the oral care composition.

The one or more polymeric solvents can comprise polyethylene glycol (PEG).

The one or more polymeric solvents can include a first polyethylene glycol (PEG) having a molecular weight of 1,500 grams per mole or less and a second polyethylene glycol (PEG) having a molecular weight of 2,000 grams per mole or greater.

The first PEG can be present in an amount of about 2% to about 15% by weight, and the second PEG can be present in an amount of about 2% to about 10% by weight, based on the total weight of the oral care composition.

The aqueous medium can be present in an amount of about 3% to about 12% by weight, based on the total weight of the oral care composition.

The composition further can comprise one or more opacifiers in a total amount of about 0.02% to about 2% by weight based on the total weight of the composition.

The opacifier can include titanium dioxide.

The film can be configured to dissolve substantially completely in contact with oral mucosa in a time of about 15 minutes to about 120 minutes.

In one or more embodiments, the present disclosure further can relate to a method of making an oral care composition comprising at least benzocaine as an active agent. Such method can comprise: solubilizing one or more active agents in one or more polymeric solvents while heating to a temperature of about 50° C. to about 120° C. to form a premix, the one or more active agents including at least benzocaine; mixing into the premix each of the following components to form a liquid composition: one or more film forming polymers; one or more bioadhesive agents; one or more plasticizers; and water; coating the liquid composition onto a backing sheet to form a layer of the composition having a thickness of about 100 µm to about 500 µm; and drying the layer to form a film of the oral care composition having a total water content of about 5% to about 15% by weight based on the total weight of the film. In further embodiments, the method of preparing the oral care composition may be defined in relation to any one or more of the following statements, which can be combined in any order and number.

The film of the oral care composition can comprise: a total of about 2% to about 35% by weight of the one or more active agents including at least benzocaine; a total of about 5% to about 20% by weight of the one or more polymeric solvents: a total of about 40% to about 80% by weight of the one or more film forming polymers; a total of about 0.5% to about 10% by weight of the one or more bioadhesive agents; and a total of about 0.5% to about 8% by weight of the one or more plasticizers; each of the foregoing amounts being based on the total weight of the film of the oral care composition.

The drying can comprise applying heated air to the layer of the composition on the backing sheet for a time of about 15 minutes to about 150 minutes.

The heated air can be applied only from above the layer of the composition.

The drying can be carried out by passing the layer of the composition on the backing sheet through a drying tunnel.

The method further can comprise cutting the film of the oral care composition into individual strips having a width of about 10 mm to about 20 mm and having a length of about 20 mm to about 30 mm.

DETAILED DESCRIPTION OF THE INVENTION

The present disclosure now will be described more fully hereinafter. The disclosure may be embodied in many different forms and should not be construed as limited to the embodiments set forth herein; rather, these embodiments are provided so that this disclosure will satisfy applicable legal requirements. Like numbers refer to like elements throughout. As used in this specification and the claims, the singular forms "a," "an," and "the" include plural references unless the context clearly dictates otherwise.

The present invention is directed to compositions comprising at least benzocaine as an active agent, the compositions being configured for formation of thin films. The formed thin films are mucoadhesive, pliable, orally soluble, and adapted for delivery of one or more active ingredients to an oral surface over a prolonged period of time. In particular, the thin films are suitable for providing delivery of benzocaine and optionally one or more similar active ingredient (e.g., menthol) that is adapted for providing temporary pain relief in an area of the oral cavity, such as the tooth and/or gums in relation to a toothache and/or to an area of the mouth in relation to a mouth sore. The thin film can be sized to be able to cover a suitably large area of the oral surface in order to provide the localized delivery of the active ingredient without substantial migration of the active ingredient to other portions of the oral cavity. Thus, the thin films provide targeted delivery of the active ingredient to achieve a more gradual coverage and longer duration of action to the intended purpose—e.g., pain relief.

In one or more embodiments, the present disclosure can provide oral care compositions comprising at least benzocaine as an active agent. Such oral care compositions can be provided in a variety of forms, such as liquids, pastes, putties, pastilles, sheets, and films. In preferred embodiments, the oral care compositions are provided in substantially solid forms with a substantially uniform shape, such as pastilles, sheets, and films. The oral care compositions preferably can be a solid or semi-solid composition up to a temperature of at least 40° C. Pastilles, sheets, and films can each be similarly configured as having a length and a width that is substantially greater than a thickness thereof. For example, pastilles can be thicker than sheets while sheets can be thicker than films. In any case, it is preferred that the oral care composition can be applied to an area of the oral cavity so that the oral care composition will be in the form of a substantial solid after application to the area of the oral cavity. Thus, the oral care composition may be provided in a liquid form that may be applied to rapidly form a solid. Preferably, the oral care composition is provided in a substantially solid form before application to the area of the oral cavity to provide for simplified application by the user. The oral care composition, being in a substantially solid form after application to the area of the oral cavity, can be configured to dissolve over time to release an active ingredient locally at the site of application in the oral cavity. Dissolution time can vary as otherwise described herein. In particularly preferred embodiments, the oral care composition is provided in the form of a film having a thickness of about 50 µm to about 500 µm, about 100 µm to about 350 µm, or about 125 µm to about 250 µm. In some embodiments, the film can have a thickness of about 500 µm or less, about 400 µm or less, about 300 µm or less, or about 200 µm or less. In such cases, it is understood that the film has a minimum thickness that is greater than 0. In an exemplary embodiment, such minimum thickness can be about 50 µm. The film can be provided in the form of strips having a width and length that provide for ease of application to the area of the oral cavity, ease of handling generally, and sufficiently broad area of coverage in the oral cavity to provide sufficient local delivery of the active agent. For example, the film can have a width of about 5 mm to about 25 mm, about 10 mm to about 20 mm, or about 12 mm to about 18 mm. The film can have a length of about 10 mm to about 850 mm, about 15 mm to about 60 mm, about 15 mm to about 35 mm, about 20 mm to about 30 mm, or about 22 mm to about 28 mm. Similar sizing may be applied to other solid forms, such as pastilles and sheets. It is understood, however, that when the oral care composition is in forms having a greater thickness, the width and/or length of the oral care composition may be lesser than when in the form of a film in order to deliver a substantially equal amount of the active agent to the local area of the oral cavity.

In one or more embodiments, an oral care composition comprising at least benzocaine as an active agent according to the present disclosure specifically can comprise one or more film forming polymers. The film forming polymer(s) can be specifically configured to cause the oral care composition to take on the desired solid form when dried to a sufficiently low water content. For example, the desired solid form can be a film in preferred embodiments as defined above, or may be a sheet or pastille form having a thickness that is greater than the thickness of a film. Examples of suitable film forming polymers include polyvinylpyrrolidones, polysaccharides, and cellulose derivatives. Other known film forming polymers may be used in combination with or as a replacement for any of the foregoing. In preferred embodiments, however, it has been found that particularly suitable films can be prepared when the oral care composition comprises one or more polymers selected from the group consisting of a polyvinylpyrrolidone, pullulan, hydroxypropyl cellulose, pectin, starch, alginic acid or a derivative thereof, and combinations thereof. Suitable alginic acid derivatives includes salts of alginic acid, such as alginates. Suitable cellulose derivatives include carboxyalkyl cellulose or a salt thereof and hydroxyalkyl cellulose or a salt thereof, in which the alkyl group of the carboxyalkyl cellulose or the hydroxyalkyl cellulose is independently selected from $C_{1-5}$ alkyl, preferably methyl, ethyl or propyl. In some embodiments, only a single film forming polymer may be utilized. In further embodiments, it can be useful to use a combination of two film forming polymers, three film forming polymers, or even more film forming polymers. Preferably, the film forming polymer can include at least pullulan, at least a polyvinylpyrrolidone, or at least both of pullulan and a polyvinylpyrrolidone.

The film forming polymer(s) can be present in a total amount of about 40% to about 80% by weight based on the total weight of the oral care composition. The total amount may be accounted for by a single film forming polymer or may be the combination of two or more film forming polymers. Preferably, the film forming polymer(s) are present in a total amount of about 45% to about 75% by weight, about 50% to about 70% by weight, or about 55% to about 65% by weight, based on the total weight of the oral care composition. In some embodiments, two film forming polymers can be used, each of which is independently present in an amount of about 20% to about 40% or about 25% to about 35% by weight based on the total weight of the oral care composition. For example, the oral care composition can comprise a polyvinylpyrrolidone in an amount of about 20% to about 40% or about 25% to about 35% by weight and also comprise pullulan in an amount of about 20% to about 40% or about 25% to about 35% by weight, based on the total weight of the oral care composition.

In some embodiments, two film forming polymers may be utilized in a defined ratio. For example, a polyvinylpyrrolidone and a polysaccharide may be combined in a ratio of 3:1 to 1:3, 2:1 to 1:2, or about 1:1. Like ratios may be utilized for any combination of two film forming polymers as described herein.

In one or more embodiments, the oral care composition comprising at least benzocaine as an active agent can comprise one or more bioadhesive agents. The bioadhesive agent(s) can be any material that is adapted to cause the oral care composition, particularly when in a solid form factor, to adhere to oral tissue, particularly oral mucosa, such as the gums. The one or more bioadhesive agents can comprise one or more of a polyacrylic acid and derivatives thereof and/or a gum. The gum may be a natural gum or a synthetic gum. The natural gum may be selected from carrageenan, tragacanth and polysaccharide gums. More preferably, when the one or more bioadhesive agents comprise a natural gum, it is tragacanth gum. The polyacrylic acid may be a high molecular weight polyacrylic acid such as a carbomer. Polymers of acrylic acid may be either crosslinked or uncrosslinked. Examples of crosslinking agents include allyl ether pentaerythritol, allyl ethers of sucrose or ally ethers of propylene. Crosslinked polymers of acrylic acid are sold under the trade name Carbopol® by Lubrizol Corporation. The polyacrylic acid derivative may be a polyacrylic acid provided as a salt, such as an ammonium, alkali metal or alkaline earth metal salt. Cross-linked polyacrylic acid, such as those cross-linked with divinyl glycol may be provided as salts such as alkaline earth metal salts, particularly calcium salts, also known as polycarbophils. Thus, the polyacrylic acid and derivatives thereof may be one or both of polycarbophil and carbomer. Any other material that is suitable for providing bioadhesive properties, particularly for providing adhesiveness to mucosal tissues, can also be used. In some embodiments, one or more components used in the present compositions for other purposes as defined herein may also provide a secondary, bioadhesive effect. For example, one or more film forming polymers (e.g., polyvinylpyrrolidones) and/or one or more polymeric solvents (e.g., PEG) may provide both the primary function as defined herein as well as providing a secondary function of bioadhesiveness. It is thus understood that use herein of the term "bioadhesive agent" relates to a material that has a primary function in the overall composition of providing bioadhesiveness. As noted, however, other components of the composition may have a secondary function of providing bioadhesiveness as well.

In some embodiments, only a single component having the primary function of a bioadhesive agent may be utilized. In further embodiments, it can be useful to use a combination of two or more components having the primary function of a bioadhesive agent. Still further, the compositions may include a single component having the primary function of a bioadhesive agent in combination with one or more components having a secondary function of bioadhesiveness. Likewise, the compositions may include two or more components having the primary function of a bioadhesive agent in combination with one or more components having a secondary function of bioadhesiveness. Preferably, the present compositions can include at least a polycarbophil as a bioadhesive agent.

The bioadhesive agent(s) can be present in a total amount of about 0.5% to about 10% by weight based on the total weight of the oral care composition. The total amount may be accounted for by a single bioadhesive agent or may be the combination of two or more bioadhesive agents. Preferably, the bioadhesive agent(s) are present in a total amount of about 0.5% to about 8% by weight, about 0.75% to about 6% by weight, or about 1% to about 5% by weight, based on the total weight of the oral care composition. In some embodiments, two bioadhesive agents can be used, each of which is independently present in an amount of about 0.25% to about 5% or about 0.5% to about 3% by weight based on the total weight of the oral care composition. For example, the oral care composition can comprise a polycarbophil in an amount of about 0.25% to about 5% or about 1% to about 4% by weight, based on the total weight of the oral care composition. It is understood that the foregoing amounts can expressly exclude the contents of other components otherwise described herein that only provide a secondary function of bioadhesiveness.

In one or more embodiment, the oral care composition comprising at least benzocaine as an active agent can comprise one or more plasticizing agents (or plasticizers). The plasticizer(s) can be any material that is adapted to impart flexibility and/or resilience to solid forms (particularly film forms) of the oral care compositions. Non-limiting examples of suitable plasticizers include polyols (e.g., glycerol, sorbitol, or sorbitan), monosaccharides, oligosaccharides, and lipids. The plasticizer(s) can be present in a total amount of about 0.5% to about 10% by weight based on the total weight of the oral care composition. The total amount may be accounted for by a single plasticizer or may be the combination of two or more plasticizers. Preferably, the plasticizer(s) are present in a total amount of about 0.5% to about 8% by weight, about 0.75% to about 6% by weight, or about 1% to about 5% by weight, based on the total weight of the oral care composition. In some embodiments, two plasticizers can be used, each of which is independently present in an amount of about 0.5% to about 5% or about 1% to about 4% by weight based on the total weight of the oral care composition. For example, the oral care composition can comprise glycerol (or another polyol) in an amount of about 0.5% to about 5% or about 1% to about 4% by weight, based on the total weight of the oral care composition.

In some embodiments, a bioadhesive agent and a plasticizer may be utilized in a defined ratio. For example, a bioadhesive agent and a plasticizer may be combined in a ratio of 3:1 to 1:3, 2:1 to 1:2, or about 1:1.

The present oral care compositions comprise at least benzocaine as an active agent. In various embodiments, one or more further active ingredients can be included in the oral care composition. The one or more further active ingredients can be configured to provide any number of desired effects. In certain embodiments, the one or more further active ingredients can be configured to provide pain relief and/or soothing and/or cooling effects. Preferably, the benzocaine and the optional one or more active ingredients can be present in an amount suitable for providing oral pain relief. The one or more additional active agents can be limited only in that it preferably is an active agent that is suitable for co-administration with benzocaine.

In some embodiments, the present oral care compositions may comprise only benzocaine as the active agent and thus may expressly exclude the presence of any further active agents. In further embodiments, the present oral care compositions may comprise benzocaine and menthol as the active agents and may expressly exclude the presence of any further active agents. In other embodiments, the oral care compositions may include an active agent that consists of benzocaine or may include active agents that consist of benzocaine and menthol or may include active agents that consist essentially of benzocaine and one or more further pain relieving agents.

The benzocaine alone or in combination with one or more further active ingredient(s) can be present in a total amount of about 2% to about 35% by weight based on the total weight of the oral care composition. The total amount may be accounted for by benzocaine or may be the combination of benzocaine with one or more further active ingredients. Preferably, the benzocaine and the optional one or more further active ingredient(s) are present in a total amount of about 5% to about 25% by weight, about 6% to about 20% by weight, or about 8% to about 18% by weight, based on the total weight of the oral care composition. In some embodiments, two active ingredients (i.e., benzocaine plus one additional active ingredient) can be used, each of which is independently present in an amount of about 1% to about 15% or about 2% to about 12% by weight based on the total weight of the oral care composition. For example, the oral care composition can comprise benzocaine in an amount of about 2% to about 15%, about 5% to about 15% by weight, or about 7% to about 12% and also comprise menthol in an amount of about 1% to about 15% or about 2% to about 8% by weight, based on the total weight of the oral care composition.

While various polymeric materials can be particularly suitable for use herein as film-forming polymers, one or more active ingredient(s) useful herein may not be particularly soluble in the film-forming polymer. Benzocaine in particular can be difficult to solubilize in various film-forming polymers. Accordingly, in various embodiments, the oral care compositions of the present disclosure further can include one or more polymeric solvents in which the one or more active agents is solubilized. The polymeric solvents can include any polymeric material in which the active ingredient exhibits higher solubility when compared to the film-forming polymer and which is suitable for intermixing with the film-forming polymer.

In order to improve solubilization of the benzocaine (and optionally menthol), it can be particularly useful for the polymeric solvent to include one or more polyalkylene glycols, wherein the alkylene group of each polyalkylene glycol is independently selected from $C_2$-$C_5$ alkylene i.e. ethylene, propylene, butylene, pentylene and the structural isomers thereof, such as n-propylene, i-propylene etc. Preferably the alkylene group is selected from ethyl or propyl. In some embodiments, the one or more polyalkylene glycols may particularly include one or more polyethylene glycols (PEG). It can be particularly beneficial to utilize two different polyalkylene glycols—i.e., at least a first polyalkylene glycol and a second polyalkylene glycol. The first polyalkylene glycol and the second polyalkylene glycol can be different in that they can differ in one or both of their molecular weight and the chain length of alkylene group. Thus, at least two polyalkylene glycols for use in the present compositions may comprise two polyalkylene glycols having the same alkylene group but different molecular weights or may comprise two polyalkylene glycols having different alkylene groups and the same or different molecular weights. The at least two polyalkylene glycols may comprise a lower molecular weight polyalkylene glycol and a higher molecular weight polyalkylene glycol. For the avoidance of doubt the terms "lower" and "higher" are relative to one another, such that the lower molecular weight polyalkylene glycol has a molecular weight that is less than a molecular weight of the higher molecular weight polyalkylene glycol, and the higher molecular weight polyalkylene glycol has a molecular weight that is higher than a molecular weight of the lower molecular weight polyalkylene glycol. In particular, it has been found according to the present disclosure that utilizing two different polyalkylene glycols can be particularly beneficial for both solubilizing the benzocaine initially and also providing stabilization of the solubilized benzocaine in the overall film composition. A first polyalkylene glycol thus improves initial solubilization of the benzocaine, and a second polyalkylene glycol improves stabilization of the solubilized benzocaine. In exemplary embodiments where different molecular weights are utilized, the polymeric solvent can comprise a first polyalkylene glycol having a first average molecular weight and a second polyalkylene glycol having a second average molecular weight. The first average molecular weight is different from the second average molecular weight. Preferably, the second average molecular weight is greater than the first average molecular weight by a factor of at least 1.5, a factor of at least 2, a factor of at least 4, a factor of at least 5, a factor of at least 8, or a factor of at least 10.

In some embodiments, a first polyalkylene glycol (particularly a first PEG) useful as a polymeric solvent can be characterized in terms of having a low molecular weight relative to the second polyalkylene glycol (particularly a second PEG). As an example, the first polyalkylene glycol (or first PEG) may have an average molecular weight of about 2,000 grams per mole or less, about 1,500 grams per mole or less, or about 1,000 grams per mole or less. Preferably, in such embodiments, the first polyalkylene glycol (or first PEG) has an average molecular weight of at least 100 grams per mole. In certain embodiments, the first polyalkylene glycol (or first PEG) may have an average molecular weight of about 100 grams per mole to about 1,000 grams per mole, about 200 grams per mole to about 800 grams per mole, or about 250 grams per mole to about 600 grams per mole. In other embodiments, the first polyalkylene glycol (or first PEG) may have an average molecular weight of about 200 grams per mole to about 2,000 grams per mole, about 250 grams per mole to about 1,500 grams per mole, or about 300 grams per mole to about 1,200 grams per mole.

In some embodiments, a second polyalkylene glycol (or second PEG) useful as a polymeric solvent can be characterized in terms of having a high molecular weight relative to the first polyalkylene glycol (or first PEG). As an example, the second polyalkylene glycol (or second PEG) may have an average molecular weight of about 2,000 grams per mole or more, about 2,500 grams per mole or more, or about 3,000 grams per mole or more. Preferably, in such embodiments, the second polyalkylene glycol (or second PEG) has an average molecular weight of no more than about 20,000 grams per mole. In certain embodiments, the second polyalkylene glycol (or second PEG) may have an average molecular weight of about 2,000 grams per mole to about 10,000 grams per mole, about 2,500 grams per mole to about 8,000 grams per mole, or about 3,000 grams per mole to about 6,000 grams per mole. In other embodiments, the second polyalkylene glycol (or second PEG) may have an average molecular weight of about 2,500 grams per mole to about 20,000 grams per mole, about 3,000 grams per mole to about 15,000 grams per mole, or about 3,500 grams per mole to about 10,000 grams per mole.

The one or more polymeric solvents preferably are present in a total amount of about 5% to about 20% by weight, based on the total weight of the oral care composition. The total amount may be accounted for by a single polymeric solvent or may be the combination of two or more polymeric solvents. Preferably, the polymeric solvent(s) are present in a total amount of about 6% to about 18% by weight, about 7% to about 16% by weight, or about 8% to about 15% by weight, based on the total weight of the oral care composition. In some embodiments, two polymeric solvents can be used, each of which is independently present in an amount of about 2% to about 15% or about 2% to about 10% by weight based on the total weight of the oral care composition. For example, the oral care composition can comprise a first polyalkylene glycol (or a first PEG) having a low molecular weight (as defined herein) in an amount of about 2% to about 15% or about 5% to about 12% by weight and also comprise a second polyalkylene glycol (or a second PEG) having a high molecular weight (as defined herein) in an amount of about 2% to about 10% or about 3% to about 8% by weight, based on the total weight of the oral care composition.

In some embodiments, two polymeric solvents may be utilized in a defined ratio. For example, when a first, low molecular weight PEG and a second, high molecular weight PEG is used, the first PEG and the second PEG may be combined in a ratio of 4:1 to 1:2, 3:1 to 1:1, or 2.5:1 to 1.5:1.

In one or more embodiments, an aqueous medium may also be utilized in forming the oral care composition. The aqueous medium preferably comprises water, more preferably substantially pure water; however, salts, buffers, or the like also may be included in the aqueous medium. In some embodiments, the aqueous medium can comprise about 0.5% to about 15% by weight, about 1% to about 14%, about 2% to about 13%, about 3% to about 12%, or about 5% to about 11% by weight of the overall oral care composition. In some embodiments, drying can be carried out to achieve a composition with an overall water or moisture content of about 1% to about 15%, about 3% to about 15%, or about 5% to about 15%, or about 5% to about 12% by weight, based on the total weight of the overall oral care composition. The water content of the oral care composition may be particularly relevant to the composition in its final form. For example, when the oral care composition is provided in a film form, it can be particularly useful for the film to be dried to a final moisture content or final water content, and such moisture content or water content can be within a range as defined above. The defined moisture level is preferred to provide the desired level of pliability and tensile strength to films formed of the composition while avoiding undesirable brittleness.

The oral care composition, in some embodiments, can include one or more opacifying agents. Suitable opacifiers can include any material suitable for causing a solid form of the oral care composition to be substantially opaque. For example, metal oxides may be utilized as opacifiers, and specific, non-limiting examples of suitable metal oxides include titanium dioxide, zinc oxide, and iron oxide. Examples of other materials suitable for use as an opacifier include magnesium carbonate, talc, and the like. One or more opacifiers, and particularly one or more metal oxides, may be included in the oral care composition in a total amount of about 0.02% to about 2% by weight, about 0.05% to about 1.5% by weight, or about 0.08% to about 1% by weight, based on the total weight of the composition.

In various embodiments, the oral care composition can further comprise one or more additional ingredients. For example, the oral care composition can comprise at least one of a pH adjusting agent, sweetener, a surfactant, a preservative, a coloring agent, a delivery enhancing polymer, and a flavoring agent.

The pH adjusting agent may be selected from the group comprising, sodium hydroxide, potassium hydroxide, citric acid, lactic acid, phosphoric acid and sodium bicarbonate. Preferably the pH adjusting agent is sodium hydroxide. Too low a pH may result in the undesirable etching of teeth. The oral composition may have a pH in the range of about 5 to about 8, about 5 to about 7.5, about 5 to about 7, or about 5 to about 6.5.

A surfactant present in the oral care compositions can be an ionic surfactant or a non-ionic surfactant. Preferably the non-ionic surfactant comprises one or more fatty acids, which may be saturated or unsaturated. More preferably the non-ionic surfactant comprises at least one unsaturated fatty acid such as oleic acid and/or linoleic acid and optionally at least one saturated fatty acid such as palmitic acid and/or stearic acid. Preferably, if present, the surfactant is provided in an amount of about 0.01% by weight to about 5% by weight based on the dry weight of the oral composition.

A polymeric compound which enhances the delivery of the active agent may also be present. Examples of such delivery enhancing polymers include copolymers of polyvinylmethylether with maleic anhydride.

In some embodiments, a sweetener can be present in an amount in the range of about 0.1% to about 1% by weight, or about 0.2% to about 0.5% by weight, based on the total weight of the oral care composition. The sweetener may be a sugar substitute, such as an artificial sugar substitute or a natural sugar substitute. The artificial sugar substitute may be selected from the group comprising sucralose, aspartame, advantame, saccharin, acesulfame potassium and cyclamate, with sucralose being preferred. The natural sugar substitute may be selected from the group comprising erythritol, mannitol, stevia, sorbitol and xylitol. Preferably the sweetener is sucralose.

In some embodiments, a flavoring agent can be present in an amount of about 0.1% to about 2% by weight, or about 0.5% to about 1% by weight, based on the total weight of the oral care composition. The flavoring agent may be an artificial flavoring or a natural flavoring. The flavoring agent may be one or more selected from the group comprising herb flavoring, such as mint, for instance spearmint or peppermint, a spice flavoring such as ginger, cinnamon or vanilla, or a fruit flavoring such as apple, grape, orange, pear or strawberry. Preferably the flavoring agent is peppermint.

In further embodiments, the oral care composition can comprise one or more preservatives. Non-limiting examples of suitable preservatives include butylated hydroxytoluene (BHT), butylated hydroxyanisole (BHA), potassium sorbate, sodium sorbate, sodium benzoate, and the like. One or more preservatives can be included in the oral care composition in a total amount of about 0.02% to about 2% by weight, about 0.05% to about 1.5% by weight, or about 0.08% to about 1% by weight, based on the total weight of the composition.

Still further, the oral care composition can include one or more natural or artificial colors as desired, preferably in an amount of 0.001% by weight to about 0.2% by weight, or about 0.01% by weight to about 0.1% by weight. The coloring agent may be, for example, FD&C blue No. 1 and like materials.

The present oral care compositions can be particularly beneficial to provide benzocaine (and optionally one or more further pain relief active ingredients) to areas of the oral cavity. In such embodiments, the present oral care compositions, particularly when on a surface of the oral cavity, are effective to deliver the pain relief active ingredient(s) for an extended duration of time. While it is desirable for the oral composition to be dissolvable within the oral cavity, the oral composition must persist in the oral cavity for a sufficient time to provide a useful effect. Preferably, the present oral composition dissolves within the oral cavity after application to a surface thereof and provides a pain-relieving effect (or other effect consistent with the mode of action of the active ingredient) for a time of at least 15 minutes, at least 30 minutes, or at least 45 minutes (e.g., up to a time of about 4 hours, up to a time of about 3 hours, or up to a time of about 2 hours). In some embodiments, the present oral composition dissolves within the mouth and provides a pain-relieving effect (or other effect consistent with the mode of action of the active ingredient) for a time of about 20 minutes to about 180 minutes, about 30 minutes to about 150 minutes, or about 45 minutes to about 120 minutes.

The ability to provide the desired effect from delivery of the active ingredient can depend upon the ability of the oral care composition to persist within the oral cavity, particularly being substantially adhered to a specific area of a surface of the oral cavity, for a sufficiently long period of time. It is generally understood that the oral care composition, when adhered to a surface of the oral cavity in a substantially solid form, will be expected to dissolve over time due to contact with saliva and/or other mucosal secretions within the oral cavity. Preferably, a solid form of the oral care composition when substantially adhered to a surface of the oral cavity can remain in a semi-solid or solid state for a time of about 5 minutes or greater, about 20 minutes or greater, about 30 minutes or greater, or about 45 minutes or greater. It is understood that the solid form of the oral care composition will be expected to substantially completely dissolve within the oral cavity within a maximum time, such as a maximum time of about 4 hours, about 3 hours, or about 2 hours. In certain embodiments, the oral care composition can remain in a semi-solid or solid state when in the oral cavity for a time of about 15 minutes to about 120 minutes, about 20 minutes to about 100 minutes, or about 30 minutes to about 90 minutes. As such, the oral care composition, when present in the oral cavity in a substantially solid form, such as a film, can be configured to dissolve substantially completely when in contact with oral mucosa in a time of about 15 minutes to about 120 minutes.

In one or more embodiments, the present disclosure further provides methods of making oral care compositions as described herein. Preferably, the methods comprise first formulating a premix that includes the benzocaine (and optionally one or more further active agents) and the one or more polymeric solvents. Specifically, this can include solubilizing the benzocaine in the one or more polymeric solvents while heating or while heating and mixing. If one or more further active agents are used, such further active agents may be added at this stage or added later with the remaining components of the composition. Solubilizing of the benzocaine with simultaneous heating and mixing can be achieved, for example, using a hotplate and a homogenizer. The combination of the benzocaine and the polymeric solvent(s) can be heated, for example, to a temperature of about 50° C. to about 120° C., about 60° C. to about 115° C., or about 70° C. to about 110° C. to form the premix. It is understood that not all active ingredients will necessitate formation of a premix. As noted above, one or more active ingredients may be included in a premix, and one or more active ingredients may be added to the main mixture.

After the premix has been formed (i.e., the benzocaine has been substantially completely dissolved in the polymeric solvent(s) used), the remaining components of the oral care composition can be mixed into the premix to form the main mixture. At a minimum, the method of preparation can comprise mixing into the premix at least one or more film forming polymers, one or more bioadhesive agents, one or more plasticizers, and water (or another aqueous solvent) to form a liquid composition. The liquid composition will be a viscous liquid, and mixing thus may be carried out using, for example, a high shear vacuum mixer to achieve mixing and degassing of the solution to form a liquid composition. Mixing is preferably carried out until a substantially homogeneous mixture is achieved and all of the components of the oral care composition have been incorporated into the solution.

The so-formed liquid composition can then be processed into the desired end form of the oral care composition. For example, the composition may be placed into molds to form pastilles or poured into cooling pans to form sheets that may be cut to desired sizes. In certain embodiments, to facilitate forming of films, the liquid composition can be coated onto a backing sheet to form a layer of the composition having the desired thickness as otherwise described herein. The backing sheet preferably is coated with a release layer, such as a wax or similar coating that will all of the formed film to be readily released therefrom. A knife or other blade may be used to coat the liquid composition to the desired thickness. Preferably, the film has a sufficient viscosity such that, after coating onto the backing sheet, the liquid composition will not substantially spread and will thus remain substantially consistent in thickness across the total surface of the coated liquid composition.

The liquid composition finally can be dried to the desired total water content as otherwise described herein to achieve the end product in a substantially solid form. Drying can comprise applying heated air to the layer of the composition on the backing sheet. Such heated air may be provided at a temperature that is above ambient and up to a temperature that is below the melting point of the film forming polymer(s). For example, the air can be a temperature of about 30° C. to about 60° C. If desired, ambient temperature air or even cooled air may be applied to facilitate drying of the film. The drying air may be applied for a time of about 15 minutes to about 150 minutes, about 20 minutes to about 150 minutes, or about 20 minutes to about 120 minutes. The oral care composition can be configured such that drying takes a minimum amount of time regardless of the application of drying air. Thus, while the application of the drying air can expedite drying, the film will typically take a time of at least 15 minutes, at least 20 minutes, at least 30 minutes, or at least 40 minutes to achieve the desired water content and thus be a self-supporting, solid composition that is no longer tacky and may be further processed for packaging of the product. In particular, drying may require a time of about 15 minutes to about 240 minutes, about 30 minutes to about 220 minutes, about 45 minutes to about 200 minutes, or about 60 minutes to about 150 minutes. In some embodiments, the drying air may be applied only from above the layer of the composition and, as such, application of air from below the layer of the composition (i.e., application of air to the backing layer) may be excluded. As a non-limiting example, drying of the film may be carried out by passing the layer of the composition on the backing sheet through a drying tunnel. In such tunnel, drying air may be applied along the entire length of the drying tunnel or only at a portion of the tunnel. Drying air may be forced air (e.g., provided via fans or blowers). In some embodiments, convection heating may be used for drying. As such, heating elements above the film layer may generate convective currents that facilitate drying of the film.

After the film has dried, the film may be cut to desired dimensions. For example, this may comprise cutting the film of the oral care composition into individual strips having a width of about 10 mm to about 20 mm and having a length of about 20 mm to about 30 mm. Cutting to other dimensions as otherwise described herein is also encompassed. The individual film strips may be packaged as desired into containers with a defined number of strips per package.

The oral composition or film obtainable by the method of making disclosed herein may be used in a method of administering benzocaine (and optionally one or more further active agents) to an oral or buccal cavity. The method can comprise at least the step of applying the oral composition obtained as described herein to a portion of an oral or buccal cavity. In further embodiments, the oral composition may first be released from its sterile packaging. Subsequently, any backing sheet is removed, for instance by peeling the oral composition or film from the backing sheet. Once the oral composition is free from any other layers, it may be applied to a portion of an oral or buccal cavity.

Embodiments of the presently disclosed oral care composition were subjected to consumer acceptability testing to evaluate effectiveness and desirability of the product. Specifically, adults who had recently used a topical toothache medication during the preceding six months were asked to use the present oral care composition in a film form and provided comments thereon. Results of such testing showed high consumer acceptability of the present oral care composition along with the following conclusion. The present oral care composition provides a soothing effect and is comfortable to use in the oral cavity. In addition to delivering pain relieving medication, the oral care composition films were found to provide a soft, comfortable barrier for an aching tooth or mouth sore. This created an advantageous difference over known, topical analgesics used for dental or mouth pain. Whereas known topical analgesics for oral use have been found to produce numbness over substantially the entire mouth, tongue, and throat due to their dislocation from the point of application and/or excessive dripping, the present oral care compositions overcome such problem by remaining substantially in place once adhered to a localized site within the oral cavity. As such, only localized numbing is provided to the actual area of application with minimal numbing effect to other areas of the oral cavity. Solid forms of the present oral care composition, such as films in particular, can be easily molded and applied over the area of the oral cavity where pain relief is needed. The film easily adheres to the tooth, gum, or other oral mucosal surface and thereby provides immediate relief and the maximum level of analgesic active ingredient to be delivered to the pain site. To this end, the film is preferably configured to be repositionable for a minimum period of time to allow for ease of application. For example, the film can be repositionable for a time of up to 2 minutes, such as about 5 seconds to about 2 minutes, about 10 seconds to about 1 minute, or about 15 seconds to about 45 seconds. Repositionable means that the film can be removed and reapplied or can be slid along the oral surface without substantial tearing or other degradation of the film. Once the film has adhered to the oral surface and is no longer considered repositionable, the film is substantially unable to be moved or removed and reapplied without tearing or otherwise destroying the film. Preferably, once the oral care composition film has been applied and adhered to the surface of the oral cavity, the film remains in place for the duration of effectiveness of the product (i.e., until complete dissolution of the product), and the film is not dislodged from its location by activities such as talking or drinking.

Example

Table 1 below provides ingredients included in an embodiment of the oral care composition of the present invention. The ingredients are listed by order of addition. Table 1 also includes the weight percentage of each ingredient, based on the total weight of the oral care composition. The primary function of each ingredient is also included.

TABLE 1

Oral Care Composition Formula 1

| Batch | Ingredient | Function | Weight Percentage |
|---|---|---|---|
| Premix | PEG 400 | Polymeric solvent | 2-15 wt. % |
| Premix | PEG 4000 | Polymeric solvent | 2-10 wt. % |
| Premix | Benzocaine | Active agent | 5-15 wt. % |
| Main | Polyvinylpyrrolidone | Film forming polymer | 20-40 wt. % |
| Main | Pullulan | Film forming polymer | 20-40 wt. % |
| Main | Polycarbophil | Bioadhesive agent | 0.75-9 wt. % |
| Main | Glycerol | Plasticizer | 0.5-8 wt. % |
| Main | Menthol | Active agent | 2-8 wt. % |
| Main | Potassium sorbate | Preservative | 0.2-2 wt. % |
| Main | Titanium dioxide | Opacifier | 0.2-2 wt. % |
| Main | Brilliant Blue | Colorant | 0.001-0.02 wt. % |
| Main | Water | Solvent | 0.05-15 wt. % |

Many modifications and other embodiments of the disclosure will come to mind to one skilled in the art to which this disclosure pertains having the benefit of the teachings presented in the foregoing description; and it will be apparent to those skilled in the art that variations and modifications of the present disclosure can be made without departing from the scope or spirit of the disclosure. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An oral care composition comprising:
   one or more film forming polymers in a total amount of about 40% to about 80% by weight;
   one or more bioadhesive agents in a total amount of about 0.5% to about 10% by weight;
   one or more plasticizers in a total amount of about 0.5% to about 8% by weight;
   one or more active agents in a total amount of about 2% to about 35% by weight, said one or more active agents including benzocaine;
   one or more polymeric solvents in which the one or more active agents is solubilized, the one or more polymeric solvents comprising a first polyalkylene glycol in an amount of about 2% to about 15% by weight, the first polyalkylene glycol having an average molecular weight of about 1,500 grams per mole or less, and a second polyalkylene glycol in an amount of about 2% to about 15% by weight, the second polyalkylene glycol having an average molecular weight of about 2,000 grams per mole or greater; and
   an aqueous medium in an amount of about 0.5% to about 15% by weight;
   each of the foregoing amounts being based on the total weight of the oral care composition;
   wherein the oral care composition is in the form of a film having a thickness of about 50 μm to about 500 μm.

2. The oral care composition of claim 1, wherein the one or more film forming polymers comprises one or more of a polyvinylpyrrolidone, a polysaccharide, and a cellulose derivative.

3. The oral care composition of claim 1, wherein the one or more film forming polymers is selected from the group consisting of a polyvinylpyrrolidone, pullulan, hydroxypropyl cellulose, pectin, and combinations thereof.

4. The oral care composition of claim 1, wherein the one or more film forming polymers includes a polyvinylpyrrolidone in an amount of about 20% to about 40% by weight and pullulan in an amount of about 20% to about 40% by weight, based on the total weight of the oral care composition.

5. The oral care composition of claim 1, wherein the one or more bioadhesive agents comprises a polycarbophil.

6. The oral care composition of claim 1, wherein the one or more plasticizers includes glycerol in an amount of about 0.25% to about 5% by weight, based on the total weight of the oral care composition.

7. The oral care composition of claim 1, wherein the one or more active ingredients further includes menthol.

8. The oral care composition of claim 1, wherein the one or more active ingredients includes benzocaine in an amount of about 2% to about 15% by weight and menthol in an amount of about 2% to about 20% by weight based on the total weight of the oral care composition.

9. The oral care composition of claim 1, wherein the one or more polymeric solvents comprises one or more different polyalkylene glycols.

10. The oral care composition of claim 1, wherein the first polyalkylene glycol is a first polyethylene glycol (PEG) having a molecular weight of 1,500 grams per mole or less, and the second polyalkylene glycol is a second polyethylene glycol (PEG) having a molecular weight of 2,000 grams per mole or greater.

11. The oral care composition of claim 10, wherein the first PEG is present in an amount of about 2% to about 15% by weight, and the second PEG is present in an amount of about 2% to about 10% by weight, based on the total weight of the oral care composition.

12. The oral care composition of claim 1, wherein the aqueous medium is present in an amount of about 3% to about 12% by weight, based on the total weight of the oral care composition.

13. The oral care composition of claim 1, wherein the composition further comprises one or more opacifiers in a total amount of about 0.02% to about 2% by weight based on the total weight of the composition.

14. The oral care composition of claim 13, wherein the opacifier includes titanium dioxide.

15. The oral care composition of claim 1, wherein the film is configured to dissolve substantially completely in contact with oral mucosa in a time of about 15 minutes to about 120 minutes.

* * * * *